United States Patent [19]

Kamoto

[11] 4,309,661
[45] Jan. 5, 1982

[54] DEVICE FOR MEASURING QUANTITY OF ELECTRIC CHARGES ON ELECTRIFIED FLUID

[75] Inventor: Satoru Kamoto, Amagasaki, Japan

[73] Assignee: Mitsubishi Denki Kabushiki Kaisha, Tokyo, Japan

[21] Appl. No.: 82,590

[22] Filed: Oct. 9, 1979

[51] Int. Cl.³ .................. G01N 27/60; G01R 29/12; H05F 1/00

[52] U.S. Cl. ........................... 324/453; 137/551; 324/454

[58] Field of Search .............. 324/72, 453, 454, 61 R; 137/551; 361/215

[56] References Cited

U.S. PATENT DOCUMENTS

| | | | |
|---|---|---|---|
| 2,315,805 | 4/1943 | Mayo et al. | 324/453 X |
| 2,491,445 | 12/1949 | Cunningham et al. | 324/71 X |
| 3,306,320 | 2/1967 | Bond | 324/453 X |
| 3,405,722 | 10/1968 | Carruthers et al. | 324/453 X |
| 3,502,965 | 3/1970 | Gerdes et al. | 324/453 |
| 4,194,148 | 3/1980 | Ohkubo | 324/453 |
| 4,258,736 | 3/1981 | Denbow | 137/551 X |

FOREIGN PATENT DOCUMENTS 524130 11/1976 U.S.S.R. ............................ 324/453

OTHER PUBLICATIONS

Klinkenberg et al., "Electrostatics in the Petroleum Industry", Elsvier Pub. Co., N.Y., 1958, pp. 123, 124.

Primary Examiner—Gerard R. Strecker
Attorney, Agent, or Firm—Wenderoth, Lind & Ponack

[57] ABSTRACT

An electrified fluid flows through a main pipe and its bypass line including a conducting pipe insulated from the remaining pipes and the main pipe. While the electrified fluid flows through the insulating pipe the latter acquires all electric charges which is, in turn, measured, as a current, by an ammeter connected between the insulated pipe and ground. A flow meter is disposed in the bypass line on the outgoing side of the insulated pipe and measures a flow rate. An electric charge density is calculated from the measured current and flow rate.

8 Claims, 4 Drawing Figures

DEVICE FOR MEASURING QUANTITY OF ELECTRIC CHARGES ON ELECTRIFIED FLUID

BACKGROUND OF THE INVENTION

This invention relates to a device for measuring the quantity of electric charges on an electrified fluid and more particularly to such a device used with electrically nonconducting fluid, for example, petroleum.

When an electrically nonconducting fluid such as petroleum is accumulated in a reservoir after flowing through a pipe line, electric charges occur in the fluid due to friction between particles thereof and between the fluid and the adjacent pipe wall. When the fluid thus electrified is accumulated in the reservoir, the sum of electric charges amounts to a considerable quantity. If the electric charges discharge within the reservoir for any reason, this may result in an accident such as an explosion. Therefore it is required to measure the total quantity of electric charges and prevent the occurrence of such an accident by using a charge neutralizer or any other means. This results in the necessity of measuring the quantity of electric charges on electrified flowing fluids.

To this end, there has been already been developed what is called a probe method. The probe method uses, as a probe, a small metallic sphere connected to an electrostatic voltmeter. When the sphere is placed in an electrified fluid to be measured, it acquires electric charges until its potential is equal to that of the fluid. Then the potential of the fluid is measured by the electrostatic voltmeter and the quantity of electric charges in the fluid is calculated. However, from other precise experiments it has been found that conventional probe methods such as described above do not give an accurate potential of the sphere particularly with flowing fluids of low electric conductivity. This is because the particular flowing fluid collides violently with the sphere resulting in great friction therebetween until electric charges are developed on the sphere itself. Also there have been the disadvantages that electrostatic voltmeters are, in many cases expensive and can not carry out an accurate measurement unless experts handle them.

Accordingly, it is an object of the present invention to provide a new and improved device for simply measuring a quantity of electric charges in a flowing electrified fluid with a high accuracy.

SUMMARY OF THE INVENTION

The present invention provides a device for measuring the quantity of electric charges in an electrified fluid comprising a main pipe, a bypass pipe line connected across one section of the main pipe, an electrically nonconducting, electrified fluid flowing through both the main pipe and the bypass pipe line, the bypass pipe line including one portion formed of an electrically conductive pipe electrically insulated from the pipe system and having a sufficiently long length, the electrically insulated pipe absorbing almost all of electric charges on the electrified fluid portion flowing therethrough, first measuring means for measuring the electric charges absorbed by the electrically insulated pipe, as a current, and second measuring means disposed in the bypass pipe line to measure the flow rate of the electrified fluid portion flowing through the bypass pipe line.

BRIEF DESCRIPTION OF THE DRAWINGS

The present invention will become more readily apparent from the following detailed description taken in conjunction with the accompanying drawings in which.

DESCRIPTION OF THE PREFERRED EMBODIMENTS

Figure 1:
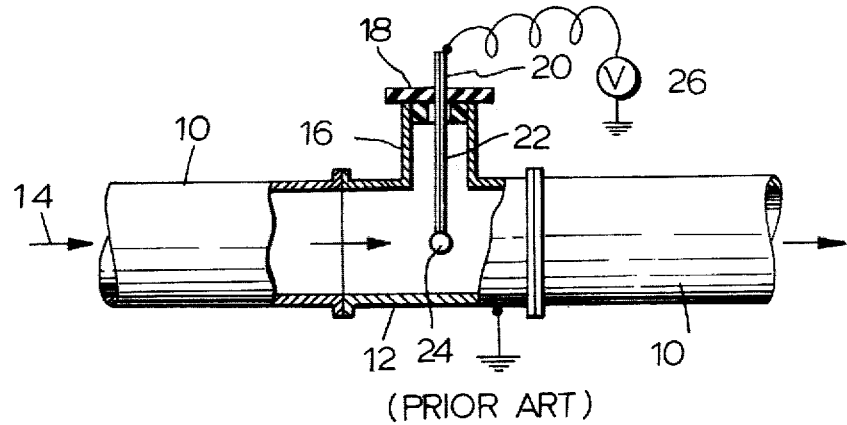
FIG. 1 is an elevation view, partly broken away, of a conventional device for measuring the quantity of electric charges in an electrified fluid by using a probe method previously employed.

Referring now to FIG. 1 of the drawings there is illustrated a conventional device for measuring the quantity of electric charges on an electrified fluid. The arrangement illustrated employs the so-called probe method as outlined above and comprises a pair of spaced pipes 10, and a metallic joint pipe 12 equal in inside diameter to the pipes 10 and interposed between the spaced pipes 10 by having both flanged ends thereof connected to adjacent flanged ends of the two pipes 10. Then an electrified fluid 14 flows through the pipes 10 and 12 in the direction of the arrow shown in FIG. 1. The joint pipe 12 is connected to ground and includes a branch pipe 16 extending perpendicularly therefrom and including an open end into which an electrically insulating flanged plug 18 is snugly fitted. A supporting rod 20 extends centrally through and is sealed in the electrically insulating plug 18 and includes a central electrical conductor 22 surrounded by an electrically insulating sleeve. The central conductor 22 includes a small metallic sphere 24, as a probe, connected to that end thereof located within the joint pipe 12. As shown in FIG. 1, the sphere 24 is located on the longitudinal axis of the joint pipe 12 and is electrically connected to an electrostatic voltmeter 26.

When the electrified fluid 14 flows through the interconnected pipes 10 and 12, the surface of the metallic sphere 24 acquires electric charges included in the flowing electrified fluid 14 until the sphere 24 has a potential equal to that of the fluid 14 due to the electric charges in the electrified fluid 14. The potential of the sphere 26 is measured by the electrostatic voltmeter 26.

Assuming that D designates the inside diameter of the pipes 10 and therefore the joint pipe 12, Q the electric charge density of the electrified fluid 14 and ε designates the dielectric constant thereof, the potential V of the sphere 24 may be expressed by $$V = (D^2/16\epsilon)Q \tag{1}$$

As described above, this potential V is measured by the electrostatic voltmeter 26. Therefore the electric charge density Q can be calculated by using the above expression (1).

However, a conventional measuring device such as shown in FIG. 1 does not indicate the accurate potential which has been found from other precise experiments conducted for making the same measurement as described above. This is considered to result principally from two factors one of which is the electric insulation and the other of which is the electrostatic charge of the metallic sphere itself. More specifically, the first factor concerns the electric insulation of the electrically insulating sleeve surrounding the central conductor 7 connected to the metallic sphere 24, the electrically insulating plug 18 and the electrostatic voltmeter 26. If those components are not in a perfect electrically insulated state then the potential can not be accurately measured by the electrostatic voltmeter 16. The second factor is most remarkable and results from the fact that, when the electrified fluid 14 flows at a high speed through the pipes 10 and 12, it strikes violently against the metallic sphere 24 and generates a large amount of friction therebetween to generate electric charges on the metallic sphere 24 itself. When the fluid 14 has a low electric conductivity, the quantity of electric charges generated on the sphere becomes quite large. Also there have been the disadvantages that the electrostatic voltmeter is usually expensive and can not carry out an accurate measurement unless an expert handles the same.

Figure 2:
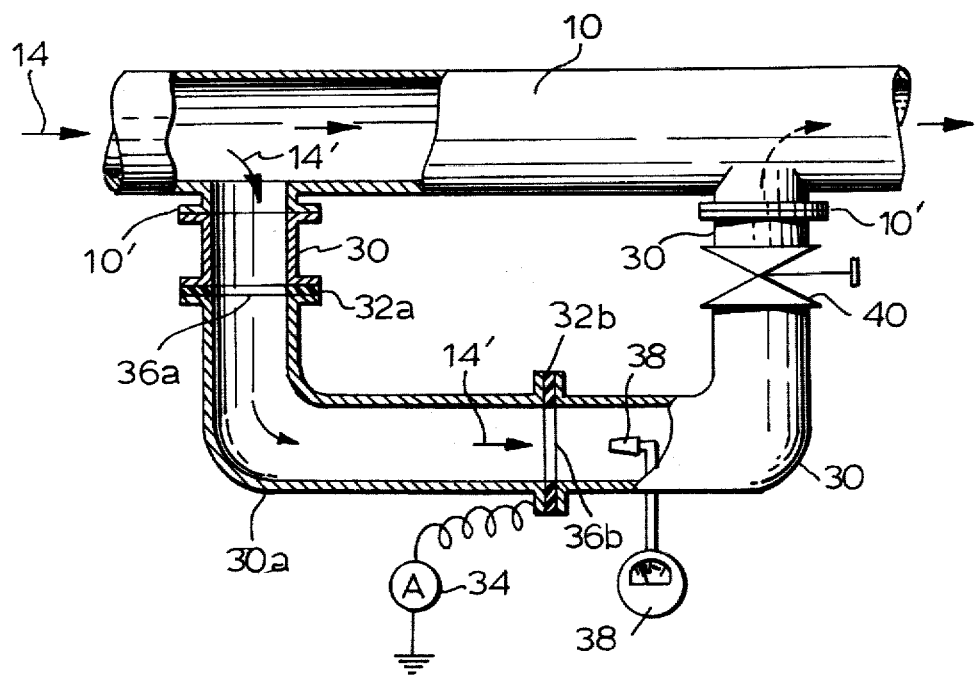
FIG. 2 is an elevation view, partly broken away, of one embodiment of a device for measuring the quantity of electric charges on an electrified fluid in accordance with the present invention.

Referring now to FIG. 2, there is illustrated one embodiment of a device for measuring the quantity of electric charges in an electrified fluid in accordance with the present invention. The arrangement illustrated comprises a main pipe 10 through which an electrically nonconducting, electrified fluid 14 flows in the direction of the arrow labelled 14 in FIG. 2. The main pipe 10 includes a section provided at either end with a lateral flanged opening which is, in turn, connected to one flanged end of a bypass pipe 30 at the junction 10'. In the example illustrated, the lefthand bypass pipe 30 as viewed in FIG. 2 is straight and relatively short while the other or righthand bypass pipe 30 is in the form of a bent pipe and is relatively long. Then a bent pipe 30a formed of an electrically conductive material is interposed between the pair of bypass pipes 30 and is connected at both flanged ends to the other flanged ends of the lefthand and righthand bypass pipes with respective electrically insulating spacers 32a and 32b therebetween. Therefore the bent pipe 30a is substantially electrically insulated from the main pipe 10 the bypass pipes 30 and forms a bypass pipe line for the fluid 14 with the bypass pipes 30. As a result, a portion of the charged fluid 14 flowing through the main pipe 20 flows through the bypass pipe line in the direction of the arrow labelled 14' in FIG. 2 to form a branched electrified fluid portion designated also by 14'. The pipe 30'a is called hereinafter an "electrically insulated pipe".

In FIG. 2, an ammeter 34 is shown as being connected across the electrically insulated pipe 30a and ground and the pipe 30a is shown as including an inlet 36a and an outlet 36b. A flow meter 38 is disposed downstream of the outlet 36b within the righthand bypass pipe 30 and spaced from the outlet 36b a small distance. The righthand bypass pipe 30 is provided adjacent to its outlet with a flow control valve 40 for controlling the flow rate of the branched fluid 14.

The flow meter and control valve have been disposed downstream of the outlet to avoid the possibility that they will create a charge on the fluid. If the flow meter and the control valve are disposed on the inlet side, then they will electrify the fluid. This may result in a difference in electric charge density between the liquid in the pipe 30a and liquid flowing through the main pipe 10. In such case an exact measurement is possible.

The operation of the arrangement shown in FIG. 2 will now be described. First it is assumed that in the section of the main pipe 10 from which the bypass pipes 30 open and adjacent thereto the electrified fluid 14 is maintained in a sufficiently balanced state with respect to the electric charges therein. In other words, the electrified fluid 14 flowing through the main pipe 10 has a constant electric charge density Q. Accordingly the branched electrified fluid portion 14' from the electrified fluid 14 flowing into the bypass pipe line 30-30a-30 has an electric charge density the magnitude of which is also Q. Further the electrified fluid portion 14' flowing through the bypass pipe line 30-30a-30 has a flow speed which is relatively low when compared with that developed in the main pipe 10.

This is so that any electric charge developed in the insulated pipe 30a is small and negligible as compared with the electric charge density Q considered to have been principally generated in the main pipe 10. In addition, the electrically insulated pipe 30a has a length sufficiently long with respect to the relaxation time of the electric charges that the interval between the entry of the fluid into the insulated pipe 30a and its delivery therefrom is sufficiently longer than the relaxation time of the electric charge so that the charge in the fluid can be completely absorbed by the pipe 30a.

Under these circumstances, the electrified fluid portion 14' enters the electrically insulated pipe 30a through the lefthand or inlet bypass pipe 30 and almost all of electric charges therein are absorbed by the metallic wall of the pipe 30a. Then the electric charges absorbed by that pipe wall flow to ground through the ammeter 34 connected across the pipe 30a and ground. As a result, the ammeter 34 indicates the magnitude of current I.

The fluid 14' from which the electric charges have been removed leaves the electrically insulated pipe 30a and bypass pipe 30 and enters the righthand or outlet after being measured by the flow meter 38. That is, the flow meter 38 measures the flow rate in amount per unit time of the fluid portion 14' to indicate the measured magnitude P thereof. Thereafter the fluid 14' flows through the flow control valve 40 and is returned to the main pipe 10.

The magnitudes Q, I and P as defined above are in the following relationship:

$$Q = I/P \qquad (2)$$

From the expression (2) it is seen that the electric charge density Q of the electrified fluid can be obtained directly from measured magnitudes provided by extremely simple measurement means.

By obtaining the electric charge density of an electrified fluid in the manner as described above, one can estimate the total quantity of electric charges or the total quantity of static electricity in an electrically nonconducting fluid flowing through the main pipe and accumulated in a reservoir.

Figure 3:
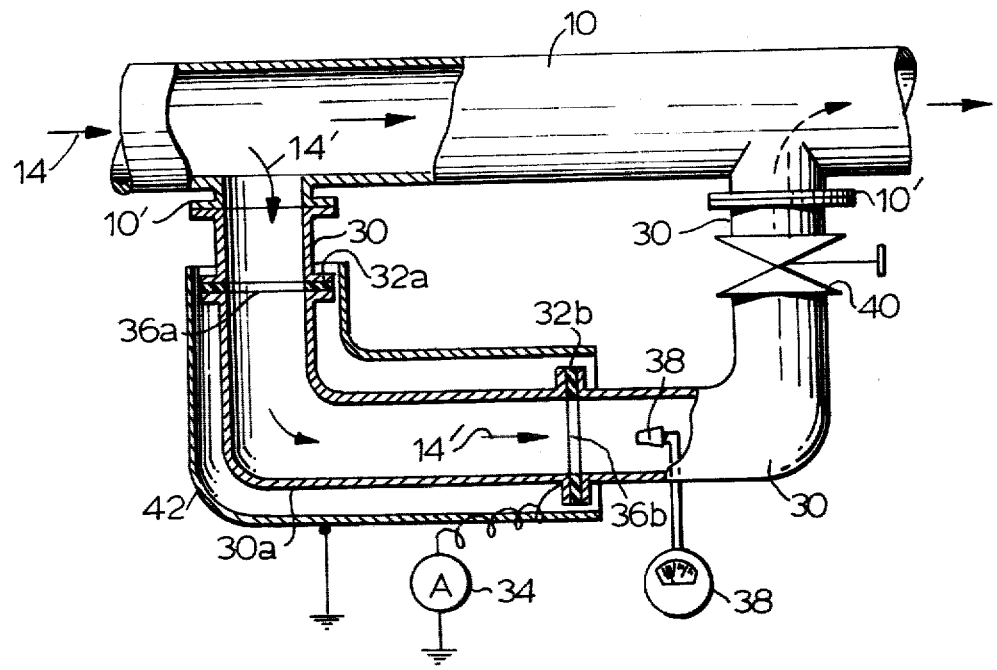
FIG. 3 is a view similar to FIG. 2 but illustrating a modification of the present invention.

The arrangement illustrated in FIG. 3 is different from that shown in FIG. 2 only in that in FIG. 3, the electrically insulated pipe 30a with the electrically insulating spacers 32a and 32b is disposed in a metallic housing 42 in the form of a bent pipe generally similar in shape to the pipe 30a and having both ends open.

Therefore like reference numerals have employed to identify the components identical to those shown in FIG. 2.

Figure 4:
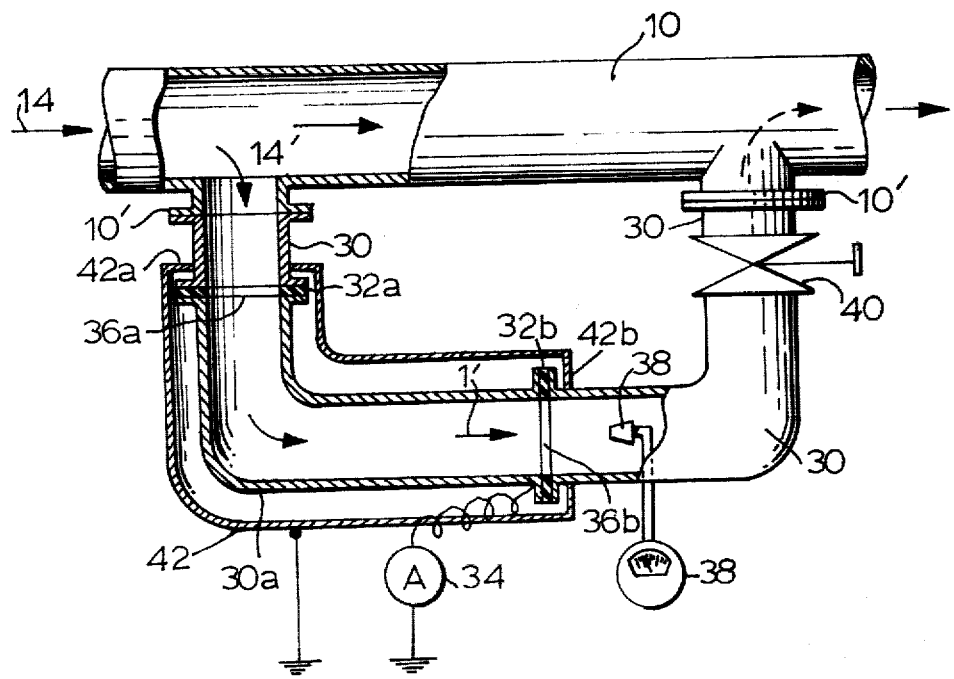
FIG. 4 is a view similar to FIG. 2 but illustrating another modification of the present invention.

In FIG. 4 wherein like reference numerals designate the components identical to those shown in FIG. 2 and 3 the housing 42 is shown as being provided at either end with a radially inwardly directed flange 42a or 42b sealed to the adjacent bypass pipe 30 to form a sealed space between the housing 42 and the electrically insulated pipe 30a. Then the space thus formed is charged with dried air or dried nitrogen.

The present invention eliminates the necessity of giving close consideration to the electrical insulation as in conventional probe methods and further of taking account of errors in measurement resulting from variations in characteristics of the probe or metallic sphere occurring depending on with the flow speed of the particular electrified fluid. Also the present invention is very advantageous in that the quantity of electric charges in electrified fluids can be accurately measured by a conventional ammeter which can be simply operated by any person without measuring the potential of the probe by an electrostatic voltmeter, which is expensive and difficult to handle.

In the arrangement of FIG. 3 it is seen that because the metallic housing encircles the electrically insulated pipe with the electrically insulating spacers therebetween, the measurement is not directly affected by external noise and rain drops and dust are prevented from adhering to the spacers. Therefore the insulation resistance of the surface of the spacers is prevented from decreasing. This makes possible an accurate measurement of minute currents.

Also in the arrangement of FIG. 4 the presence of dried air or nitrogen can improve the measurement conditions.

While the present invention has been illustrated and described in conjunction with a few preferred embodiments thereof it is to be understood that numerous changes and modifications may be resorted to without departing from the spirit and scope of the present invention. For example, the flow meter 38 and the flow control valve 40 may be replaced by a proportional pump for keeping the delivery flow rate unchanged with respect to time. This saves time required for purposely measuring the flow rate and the expression (2) can be reduced to $Q = k \cdot I$ where k is a constant. Therefore the ammeter can indicate the electric charge density.

Also if the bypass pipes 30 are formed of an electrically insulating material, then the branched electrified fluid portion 14' flows through the bypass pipes to electrify the latter due to friction occurring between the same and the walls of each pipe 30. As a result, the inlet bypass pipes 30 are put at high potentials to cause currents to flow in the electrically insulated pipe 30a resulting in the possibility of causing an error in measurement. However, when the bypass pipes 30 are formed of an electrically conductive material the potentials thereof can be reduced thereby to decrease currents flowing in the electrically insulated pipe 30a. This results in an increase in accuracy of measurement.

Further, the electrically conducting bypass pipe 30 may be connected to ground. With this measure a null current from that bypass pipe enters the electrically insulated pipe 30a. Also the potential developed on the main pipe 10 causes a current therefrom to be connected to ground through the bypass pipe 30. This prevents that current from entering the electrically insulated pipe 30a resulting in a further increase in accuracy of measurement.

What is claimed is:

1. A device for measuring the quantity of electric charge carried by an electrically insulating fluid flowing in a main pipe, comprising:
    a bypass pipe which is connected in parallel with a section of said main pipe and through which a portion of said fluid flowing in said main pipe is caused to flow, said bypass pipe comprising an electrically conductive pipe section electrically insulated from said main pipe;
    electrical conductor means connected to said conductive pipe section for electrically connecting said conductive pipe section to ground;
    current measuring means connected to said electrical conductor means for measuring the magnitude of electric current flowing in said conductor means;
    and flow measuring means disposed in said bypass pipe for measuring flow rate of said portion of the fluid flowing in said bypass pipe; and
    flow control means in said bypass pipe for controlling the flow rate of the fluid therethrough;
    said conductive pipe section having sufficient length for the electric charge carried by said portion of fluid flowing in said conductive pipe section at the flow rate as controlled by said flow control means to be absorbed by said conductive pipe section and grounded through said conductor means.

2. A device as claimed in claim 1 wherein said conductor means and said current measuring means is comprised of an ammeter, a first electric conductor connecting said conductive pipe section to a terminal of said ammeter, and a second electrical conductor connecting the other terminal of said ammeter to ground.

3. A device as claimed in claim 1, wherein said flow measuring means is a flow meter situated in said bypass pipe downstream of said conductive pipe section.

4. A device as claimed in claim 1, further comprising a flow control valve disposed in said bypass pipe downstream of said flow measuring means for controlling the flow rate of said portion of fluid flowing in said bypass pipe.

5. A device as claimed in claim 1, wherein said flow measuring means comprises a proportional pump disposed in said bypass pipe which controls the flow rate of said portion of fluid flowing in said bypass pipe to a predetermined magnitude which is fixed with respect to time.

6. A device as claimed in any one of claims 1 through 5, further comprising a grounded metallic housing within which said conductive pipe section is housed.

7. A device as claimed in claim 6, wherein said bypass pipe further comprises pipe portions adjacent to and insulated from said conductive pipe section, and said metallic housing comprises a cylindrical portion surrounding said conductive pipe section and a pair of annular end portions extending radially inward with respect to said cylindrical portion from both ends of said cylindrical portion to the outer surfaces of said pipe portions of said bypass pipe, said metallic housing and the outer surface of said bypass pipe being sealed to each other for hermetically sealing the space within said metallic housing.

8. A device as claimed in claim 7, wherein said space is filled with a gaseous material selected from the group consisting of dried air and dried nitrogen.

* * * * *